United States Patent
Kanehira et al.

(10) Patent No.: US 9,439,639 B2
(45) Date of Patent: Sep. 13, 2016

(54) MEDICAL TREATMENT TOOL

(75) Inventors: Eiji Kanehira, Tokyo (JP); Etsuro Yamabe, Akita (JP); Minoru Suzuki, Akita (JP)

(73) Assignee: SUMITOMO BAKELITE CO., LTD., Tokyo (JP)

( * ) Notice: Subject to any disclaimer, the term of this patent is extended or adjusted under 35 U.S.C. 154(b) by 163 days.

(21) Appl. No.: 14/370,871

(22) PCT Filed: Jan. 25, 2012

(86) PCT No.: PCT/JP2012/000448
§ 371 (c)(1),
(2), (4) Date: Jul. 7, 2014

(87) PCT Pub. No.: WO2013/111183
PCT Pub. Date: Aug. 1, 2013

(65) Prior Publication Data
US 2015/0238179 A1    Aug. 27, 2015

(51) Int. Cl.
*A61B 17/02* (2006.01)
*A61B 17/34* (2006.01)

(52) U.S. Cl.
CPC ....... *A61B 17/0218* (2013.01); *A61B 17/0293* (2013.01); *A61B 17/3423* (2013.01); *A61B 17/3498* (2013.01); *A61B 2017/0225* (2013.01); *A61B 2017/347* (2013.01); *A61B 2017/3449* (2013.01); *A61B 2017/3466* (2013.01); *A61B 2090/0811* (2016.02)

(58) Field of Classification Search
CPC ...................................... A61B 17/02–17/0293
USPC ........................................ 600/201, 208, 215
See application file for complete search history.

(56) References Cited

U.S. PATENT DOCUMENTS

| 8,187,178 B2 | 5/2012 | Bonadio et al. |
| 8,251,900 B2 | 8/2012 | Ortiz et al. |

(Continued)

FOREIGN PATENT DOCUMENTS

| CN | 102018568 A | 4/2011 |
| EP | 2272436 A1 | 1/2002 |

(Continued)

OTHER PUBLICATIONS

International Search Report dated Feb. 15, 2012, issued in corresponding application No. PCT/JP2012/000448.
ESSR dated Jan. 9, 2015 issued in counterpart EP Application No. 12866959, (7 pages).

*Primary Examiner* — Nicholas Plionis
(74) *Attorney, Agent, or Firm* — Westerman, Hattori, Daniels & Adrian, LLP

(57) ABSTRACT

A medical treatment tool (10) includes a retractor main body (30) and a converter (20). The retractor main body (30) forms a cylindrical shape and is placed in an incision. The converter (20) is detachably installed on an opening end (32) of the retractor main body (30) and closes the opening end (32). Ports (22a) to (22d) through which treatment tools are respectively inserted into the retractor main body (30) are provided in a plurality of sites of the converter (20). The converter (20) can be installed on the opening end (32) at an installation angle which is selected from a plurality of angles. The positional relationships of the ports (22a) to (22d) with respect to the retractor main body (30) when the converter (20) is installed on the opening end (32) at the respective installation angles become different from each other.

7 Claims, 8 Drawing Sheets

(56) References Cited

U.S. PATENT DOCUMENTS

| | | |
|---|---|---|
| 2005/0197537 A1* | 9/2005 | Bonadio ............ A61B 17/0293 600/208 |
| 2007/0225569 A1 | 9/2007 | Ewers et al. |
| 2009/0036745 A1 | 2/2009 | Bonadio et al. |
| 2010/0081880 A1* | 4/2010 | Widenhouse ...... A61B 17/3462 600/201 |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0228096 A1* | 9/2010 | Weisenburgh, II ....................... A61B 17/3423 600/214 |
| 2010/0228198 A1 | 9/2010 | Widenhouse et al. |
| 2010/0261975 A1 | 10/2010 | Huey et al. |
| 2010/0312063 A1 | 12/2010 | Hess et al. |
| 2011/0028794 A1 | 2/2011 | Widenhouse et al. |
| 2011/0112371 A1 | 5/2011 | Smith et al. |
| 2011/0152625 A1* | 6/2011 | Smith ................. A61B 17/3462 600/208 |
| 2013/0060093 A1 | 3/2013 | Bonadio et al. |

FOREIGN PATENT DOCUMENTS

| | | |
|---|---|---|
| JP | 2002-28163 A | 1/2002 |
| JP | 2002325769 A1 | 12/2002 |
| JP | 2010-207576 A | 9/2010 |
| JP | 2010-207577 A | 9/2010 |
| JP | 2010-207578 A | 9/2010 |
| JP | 2010-207579 A | 9/2010 |
| TW | 201102044 A | 1/2011 |
| WO | 2008/149332 A1 | 12/2008 |
| WO | 2010/141409 A1 | 12/2010 |

* cited by examiner

MEDICAL TREATMENT TOOL

TECHNICAL FIELD

The present invention relates to a medical treatment tool which is placed in an incision when used.

BACKGROUND ART

In laparoscopic surgery, a single hole-type surgery through which the surgery is performed by inserting a plurality of treatment tools such as forceps or optical devices through an incision has been performed. The surgery method has a great cosmetic advantage since only an incision remains on the body surface of a patient. Generally, the incision is formed in the umbilicus in order to prevent the incision from being conspicuous after the surgery.

In recent years, exclusive instruments for inserting a plurality of treatment tools in an incision has been developed (refer to Patent Documents 1 and 2). These instruments include a cylindrical retractor main body that holds the incision in an opened state and a lid-like converter having a plurality of small holes (ports) through which the treatment tools are respectively inserted.

Meanwhile, in the laparoscopic surgery, it is necessary to take an excised organ (excised tissue) outside the body. Since the excised tissue cannot pass through the port, in a case of taking out an excised tissue larger than the inner diameter of the port, the forceps holding the excised tissue have been pulled out together with the retractor main body from the incision. In addition, in a case where cancer is suspected to be present in an organ, in general, the excised tissue is collected in a collection bag in the abdominal cavity, and then, the excised tissue is taken out by pulling the collection bag together with the retractor main body from the incision in order to prevent implantation of the cancer. However, the work for pulling out the retractor main body from the incision imposes a large burden on the patient. In particular, in a case of excising a plurality of diseased areas and repeatedly taking out the tissues, it is necessary to install and remove the retractor main body many times with respect to the incision, which imposes a large burden on the patient.

In contrast to the above, in the instruments disclosed in Patent Documents 1 and 2, the converter is detachable from the retractor main body. For this reason, when taking out the excised tissue, it is possible to pull out the forceps or the collection bag through an opening of the retractor main body, the opening having a large diameter, by removing the converter from the retractor main body while placing the retractor main body in the incision. Accordingly, it is unnecessary to repeatedly attach the retractor main body to and detach the retractor main body from the abdominal wall even in the case of taking out the large excised tissue or collection bag to the outside the body. For this reason, it is possible to promptly perform excision with a small burden on the patient.

In the instrument disclosed in Patent Document 1, as shown in FIG. 1 thereof, the converter is installed in a manner such that a projection is locked to an engagement groove by rotating the converter (valve plate) around an axis with respect to the retractor main body (holder main body). In addition, in the instrument, as shown in FIG. 5(b) or FIG. 6(b) of Patent Document 1, the projections and the ports are disposed to have equal angular intervals (120 degree intervals). For this reason, the arrangement position of the ports with respect to the retractor main body can be always kept constant without particularly considering the attachment angle of the converter.

In addition, in the instrument of Patent Document 2, as shown in FIG. 10 (FIG. 11) or FIG. 16 (FIG. 17) thereof, it is possible to detachably install a converter (20), to which a plurality of ports (25 to 28) are provided, by pushing the converter to a retractor main body (2) at an arbitrary angle. Specifically, as shown in FIG. 10 of Patent Document 2, a mode of installing a connector base (80), around which a plurality of elastic projections (91) are formed, in a ring (6) in a snap manner, and a mode of inserting an O ring (53) in an engaging ring (54) as shown in FIG. 16 thereof are disclosed.

RELATED DOCUMENT

Patent Document

[Patent Document 1] Japanese Unexamined Patent Publication No. 2002-28163

[Patent Document 2] Pamphlet of International Publication No. 2008/149332

SUMMARY OF THE INVENTION

In a single hole-type surgery through which an incision is formed in the umbilicus or the like, in a case of excising a diseased area by accessing various organs such as the stomach, the gallbladder, and the large intestine through an operation under pneumoperitoneum, a plurality of ports closest to the subject diseased area are selected each time to insert forceps for holding or a scalpel for excision therethrough. In general, auxiliary forceps, optical devices and the like are inserted in the other ports.

For this reason, when detachably installing a converter on a retractor main body which is placed in an incision, it is necessary to satisfy contrary demands, which are stability of operation while repeatedly accessing a particular organ during treatment and realization of a variety of operations capable of easily accessing various organs.

However, the instrument of Patent Document 1 is reproduced in an equilateral triangle in which the arrangement position of the ports are always equal with respect to the retractor main body. Therefore, it is difficult to access diseased areas depending on the position of the diseased areas which are, for example, positioned on an extension line of two ports.

In addition, the instrument of Patent Document 2 is configured such that the converter is installed on the retractor main body at the arbitrary angle, and therefore, there is no reproducibility at the angle of mounting the converter on the retractor main body. For this reason, there is a problem in that the positional relationships between organs and ports change each time when taking out an excised tissue by removing the converter from the retractor main body many times.

The present invention is made from the viewpoint of the above-described problems and provides a medical treatment tool through which the stability of the operation while repeatedly accessing organs through the ports during the treatment and various accesses to various organs can be realized.

(1) A medical treatment tool includes: a cylindrical retractor main body which is placed in an incision; a converter which is detachably installed on an opening end of the retractor main body to close the opening end; and ports which are provided in a plurality of sites of the converter and through which treatment tools are inserted into the retractor main body, in which the converter can be installed on the opening end at an installation angle which is selected from a plurality of angles, and positional relationships of the ports with respect to the retractor main body when the converter is installed on the opening end at the respective installation angles become different from each other.

In the above-described invention, the point that the positional relationships of the plurality of ports with respect to the retractor main body are the same as each other indicates that the plurality of ports are arranged in a rotational symmetrical position and that the arrangement position of the visual aspect of the ports is not changed even if the installation angle of the converter is changed. In contrast, the point that the positional relationships of the ports with respect to the retractor main body are different from each other indicates that the arrangement position of the visual aspect of the plurality of ports changes with the retractor main body as a reference.

According to the above-described invention, minute fluctuation of a relative position between the retractor main body and the ports is prevented due to the installation angles of the converter being selective, and therefore, the arrangement position of the ports is reproduced on the retractor main body. In addition, the positional relationships of the ports with respect to the retractor main body changes by changing selection of the installation angle of the converter, and therefore, the arrangement positions of the ports are diversified.

In the medical treatment tool of the present invention, as a more specific mode, (2) the retractor main body may include an expansion unit that holds the incision in an expanded state in a predetermined opening direction, and at the plurality of the installation angles, positional relationships of the ports with respect to the incision in the opening direction may be different from each other. (3) The angle, which is formed between a perpendicular bisector of a line segment that connects a first port and a second port and the opening direction when the converter is installed on the opening end at any one or more installation angles, may be 115 degrees±20 degrees. (4) The medical treatment tool may include at least the first port to a third port disposed in an approximately equilateral triangle shape and the installation angles may be selected from four or more angles. (5) A plurality of valve members capable of inserting the treatment tools may be respectively provided in the ports. (6) The converter may include a flexible top plate portion that closes the opening end, the top plate portion may be provided with the first port and the second port, and the valve member may be made of a harder material than that of the top plate portion. (7) The medical treatment tool may further include: another port, of which the formation height of the valve member is different from the first port, on a straight line which passes through the first port and is parallel to the perpendicular bisector. (8) The medical treatment tool may further include: a locking unit that locks the converter to the retractor main body to be in a locking state by rotating the converter in an axial rotating direction with respect to the retractor main body by a predetermined angle from a non-locking state where the converter comes into contact with the opening end. (9) An indicator portion that shows an extending direction of the perpendicular bisector in the locking state may be provided further forward than the perpendicular bisector in the axial rotating direction by the predetermined angle.

In the above-described invention, the point that the positional relationships of the ports with respect to the incision in the opening direction are different from each other indicates that the arrangement position of the visual aspect of the plurality of ports changes with the operation direction of the expansion unit as a reference.

It is unnecessary that each of the elements of the present invention independently exist allowing that a plurality of elements are formed as a member, an element is formed as a plurality of members, a certain element is a portion of the other element, a portion of a certain element overlaps a portion of the other element, and the like.

According to the present invention, in a case of repeatedly accessing the organs through the ports during the treatment, it is possible to stably perform the treatment operation since the arrangement position of the ports with respect to the retractor main body is reproduced. In addition, it is possible to realize various accesses to various organs since the positional relationships between the ports changes with respect to the retractor main body by changing the selection of the installation angle of the converter.

BRIEF DESCRIPTION OF THE DRAWINGS

The above-described object and other objects, characteristics, and benefits are further clarified through favorable embodiments to be described below and the accompanying drawings.

DESCRIPTION OF EMBODIMENTS

Figure 1A:
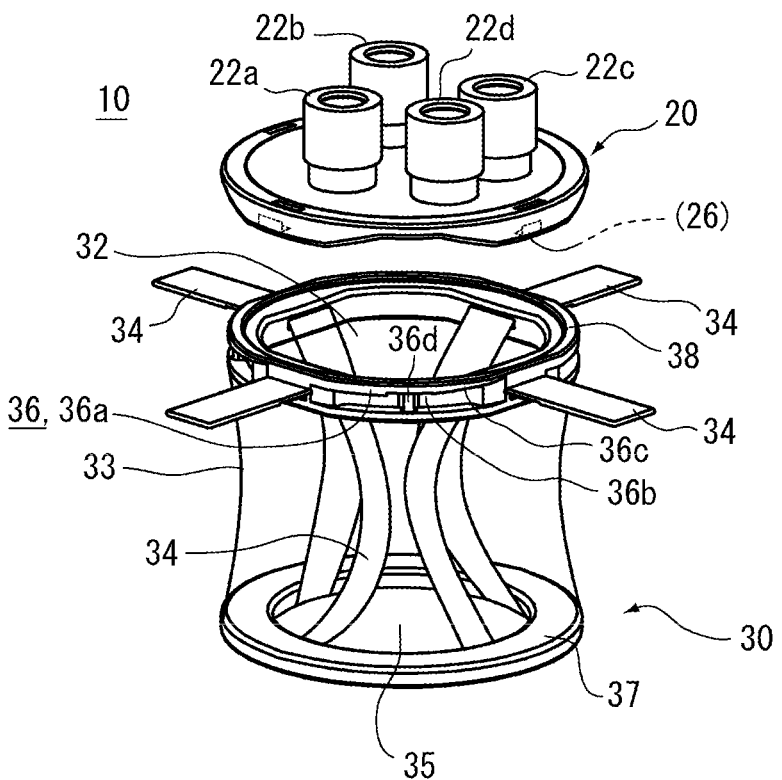
FIG. 1A is a perspective view showing a state where a converter is separated from a retractor main body.

Hereinafter, embodiments of the present invention will be described based on the drawings. In all of the drawings, the same components are given the same reference numerals and the description will not be repeated.

Figure 1B:
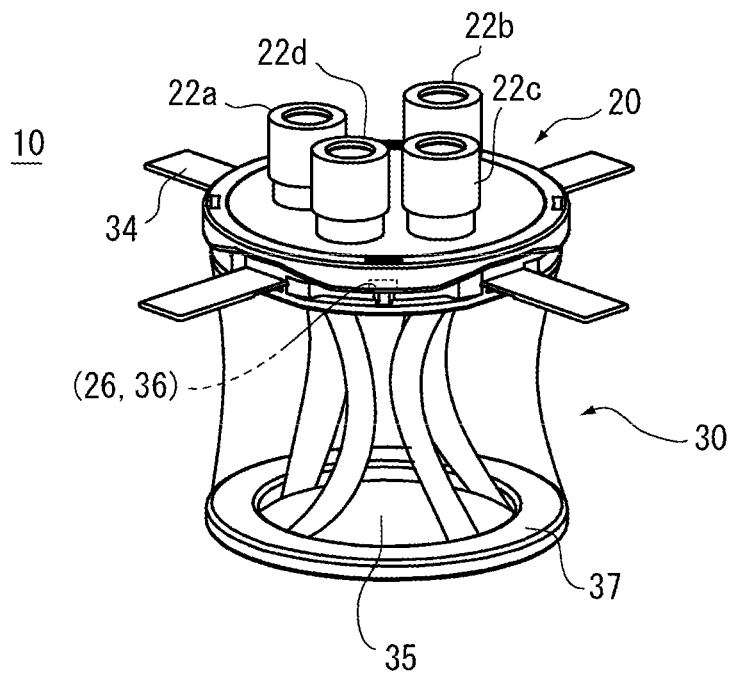
FIG. 1B is a perspective view showing a state where the converter is installed on the retractor main body.

FIGS. 1A and 1B are perspective views showing an example of a medical treatment tool 10 according to the embodiment of the present invention. More specifically, FIG. 1A shows a state where a converter 20 is separated from a retractor main body 30 and FIG. 1B shows a state where the converter 20 is installed on the retractor main body 30.

Figure 2A:
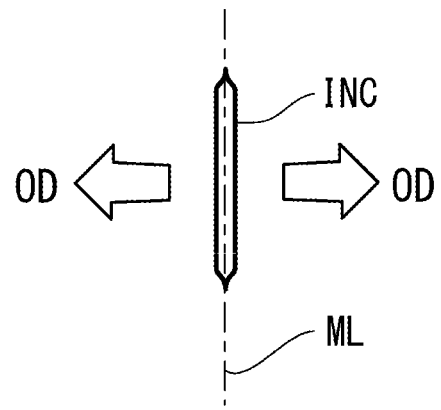
FIG. 2A is a plan view of an incision.
Figure 2B:
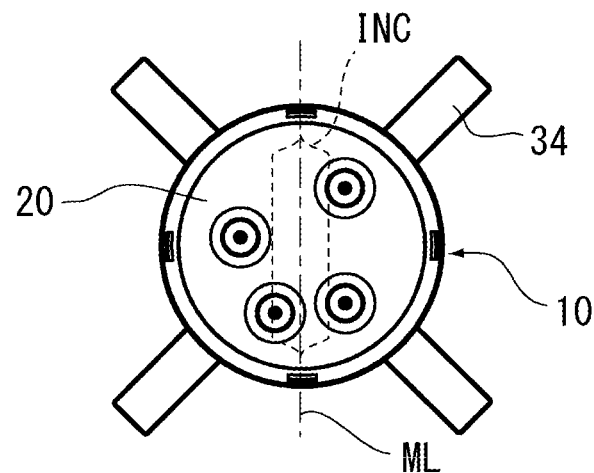
FIG. 2B is a plan view showing a state where a medical treatment tool is placed in the incision.
Figure 2C:
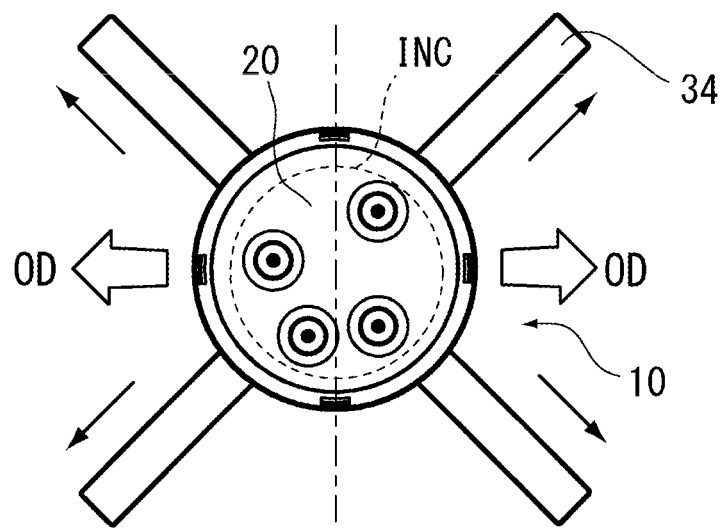
FIG. 2C is a plan view showing a state where the diameter of incision is expanded using the medical treatment tool.

FIGS. 2A to 2C are plan views showing a state where the medical treatment tool 10 of the present embodiment is placed in an incision INC. FIG. 2A is a plan view of the incision INC which is formed to pass through an umbilicus BT (which is not shown in FIG. 2A; refer to FIG. 5) along a median line ML of a patient. An opening direction OD in which the diameter of the incision INC is expanded using the medical treatment tool 10 is shown in FIG. 2A using a hollow arrow. FIG. 2B is a plan view showing a state where the medical treatment tool 10 is placed in the incision INC. FIG. 2C is a plan view showing a state where the incision INC is pulled to every side (in an arrow direction) in a radiation direction using an expansion unit (tension belt 34) of the medical treatment tool 10 to expand the diameter of the incision INC in an approximately circular shape in the opening direction OD (hollow arrow). When pulling the tension belt 34 as shown in FIG. 2C, the converter 20 may be installed on the retractor main body 30, or the tension belt 34 of the retractor main body 30 may be pulled in a state where the converter 20 is separated from the retractor main body 30.

First, an overview of the medical treatment tool 10 of the present embodiment will be described.

The medical treatment tool 10 of the present embodiment includes the retractor main body 30 and the converter 20. The retractor main body 30 forms a cylindrical shape and is placed in the incision INC. The converter 20 is detachably installed on an opening end 32 of the retractor main body 30 and closes the opening end 32. In addition, ports 22a to 22d which are installed in a plurality of sites of the converter 20 and through which treatment tools (not shown) are respectively inserted into the retractor main body 30 are provided. In the medical treatment tool 10 of the present embodiment, the converter 20 can be installed on the opening end 32 at an installation angle which is selected from a plurality of angles, and the positional relationships of the ports 22a to 22d with respect to the retractor main body 30 when the converter 20 is installed on the opening end 32 at the respective installation angles become different from each other.

Next, the medical treatment tool 10 of the present embodiment will be described in detail.

The medical treatment tool 10 is an instrument for holding in an opened state and protecting the incision INC and for supporting various treatments such as observation of the inside the abdominal cavity, washing, excision, or placement and collection of instruments.

The retractor main body 30 is a member which is installed in the incision INC so as to pinch the surface and the rear surface of the abdominal wall and which applies a force to the incision INC in a radial direction to expand the diameter of the incision. The specific configuration of the retractor main body 30 is not particularly limited, and for example, the retractor main body 30 of the present embodiment includes a cylindrical member 33 having air tightness and flexibility, a first fixing member 37 and a second fixing member 38 which are provided in both ends of the cylindrical member 33. In addition, the retractor main body 30 is provided with a plurality of tension belts 34 that reach both of the fixing members. The tension belts 34 are provided inside the cylindrical member 33.

The first fixing member 37 and the second fixing member 38 form a flat plate annular shape. The first fixing member 37 is a member which is inserted into the abdominal cavity through the incision INC and which forms the opening end 35, and the first fixing member is closely attached to the rear surface of the abdominal wall when used. The second fixing member 38 is a member that forms the opening end 32 and is closely attached to the surface (body surface) of the abdominal wall when used. The retractor main body 30 forms a cylindrical shape by coaxially connecting the cylindrical member 33 with the annular first fixing member 37 (opening end 35) and second fixing member 38 (opening end 32). Here, the cylindrical shape may be a circular cylindrical shape or a squarely cylindrical shape.

A tip end of the tension belt 34 (lower end in FIGS. 1A and 1B) is fixedly connected to the first fixing member 37. In addition, a base end of the tension belt 34 (upper end in FIGS. 1A and 1B) is inserted into the second fixing member 38 in a manner of penetrating the second fixing member 38 from the inside to the outside thereof in the radial direction. The tension belt 34 and the second fixing member 38 are respectively provided with ratchet structures (not shown) which allow the base end of the tension belt 34 to slide to the outside in the radial direction of the second fixing member 38 in a pulling-out direction, but which in contrast, restrict the base end of the tension belt 34 to slide to the inside in the radial direction in a returning direction. By pulling the base end of the tension belt 34 to the outside with respect to the second fixing member 38 in the radial direction, the first fixing member 37 is drawn up and the gap between the first fixing member and the second fixing member 38 is shortened. At this time, the cylindrical member 33 is folded on the outside of the tension belt 34 so as to have a bellows shape. If the base ends of the four tension belts 34 are pulled by the same length simultaneously or in a predetermined order, the first fixing member 37 approaches the second fixing member 38 while facing the second fixing member 38.

Here, by inserting the first fixing member 37 into the incision INC and pulling the tension belt 34 in a state where the first fixing member 37 and the second fixing member 38 gently pinch the abdominal wall, the first fixing member 37 and the second fixing member 38 are brought into close contact with the rear surface and the surface of the abdominal wall. As a result, a through hole having the opening ends 32 and 35 as both ends of the annular first fixing member 37 and the second fixing member 38 is formed inside the incision INC. An excised tissue is taken out from the inside to the outside of the body through the through hole.

In the first fixing member 37 and the second fixing member 38, resin materials such as vinyl chloride resins, polyurethane resins, polyamide resins, polyethylene resins, polypropylene resins, polyacetal resins, acrylonitrile-butadiene-styrene copolymer (ABS) resins, hydrogenated styrene-based thermoplastic elastomer (SEBS) resins, and silicone rubber; or metallic materials such as stainless steel are used.

The cylindrical member 33 is formed of a film having a thickness equal to or greater than 0.05 mm and equal to or less than 3 mm. As the materials of the cylindrical member 33, soft vinyl chloride resins, polyurethane resins, polyethylene resins, polyamide resins, polypropylene resins, polyester resins, SEBS resins, silicone rubber, natural rubber, and the like are preferable.

The converter 20 is a member which is air-tightly covers the incision INC by detachably installing the converter on the opening end 32 of the retractor main body 30 and closing the opening end. Here, the point that the converter 20 closes the opening end 32 means that the converter 20 is provided in the side of the opening end 32 rather than in the side of the cylindrical member 33. Moreover, the point that the converter 20 is detachable means that the converter 20 can be installed on or taken out from the retractor main body 30 in a state where the retractor main body 30 is placed in the abdominal wall.

Figure 3A:
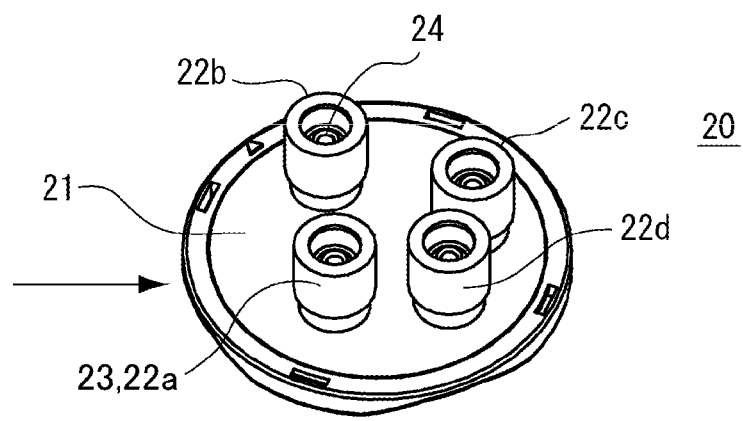
FIG. 3A is a perspective view of the converter when seen from above.
Figure 3B:
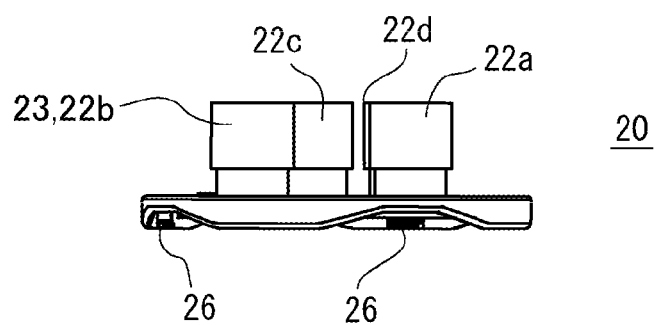
FIG. 3B is an arrow view of FIG. 3A.
Figure 3C:
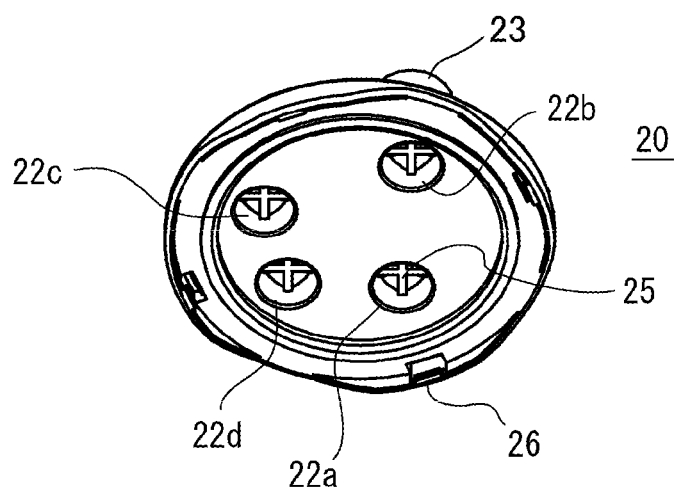
FIG. 3C is a perspective view of the converter when seen from below.

FIG. 3A is a perspective view of the converter 20 when seen from above. FIG. 3B is an arrow view of FIG. 3A. FIG. 3C is a perspective view of the converter 20 when seen from below.

The converter 20 includes a top plate portion 21, a plurality of ports 22a to 22d which are formed to project from the top plate portion 21, and a plurality of engagement projections 26 which are formed around the top plate portion 21. The converter 20 of the present embodiment forms an approximately circular shape in a plan view and the engagement projections 26 are formed in four sites at intervals of 90 degrees. The engagement projections 26 are projection pieces formed to project to the inside of the converter 20 in the radial direction.

The top plate portion 21 is a member closing the opening end 32 in the side of the upper (proximal) end of the retractor main body 30. The ports 22a to 22d are provided in the top plate portion 21. The ports 22a to 22d are formed of a cylindrical portion 23 and valve members 24 and 25. The cylindrical portion 23 is formed to project from the top surface of the top plate portion 21. The lower end of the cylindrical portion 23 is continuously connected to the ports 22a to 22d. Treatment tools such as forceps or scalpel are inserted from the upper end of the cylindrical portion 23. Valve members 24 and 25 are provided inside the cylindrical portion 23. Either or both of the valve members 24 and 25 are closely attached to the periphery of a treatment tool inserted into the cylindrical portion 23. Accordingly, leakage of gas filling the abdominal cavity from the ports 22a to 22d during the handling of the treatment tools is suppressed.

The periphery of the annular second fixing member 38 of the retractor main body 30 is provided with a locking portion 36 configuring a locking unit of the converter 20. The locking portion 36 is formed of a locking piece 36a, a notched recess 36b, and a slope portion 36c. The locking piece 36a is a projection piece adjacent to the notched recess 36b which is partially notched in the peripheral surface of the second fixing member 38. In addition, the locking piece 36a is a part that locks the converter 20 by coming into contact with the engagement projection 26 in a circumferential direction. The slope portion 36c is formed in an opposite side of the locking piece 36a with respect to the notched recess 36b. The slope portion 36c is a projection piece formed in the peripheral surface of the second fixing member 38 and is inclined downward in an axial direction. The notched recess 36b is formed at a lowermost position of the slope portion 36c through a discontinuous step.

The locking portion 36 (locking piece 36a) is formed at a position corresponding to the engagement projection 26. Specifically, the locking portion 36 is formed in four sites of the periphery of the second fixing member 38 at intervals of 90 degrees. In addition, in the notched recess 36b, a reinforcement rib 36d is formed to project outward in the radial direction.

As described later using FIG. 7, in the medical treatment tool 10 of the present embodiment, when the converter 20 is screwed with respect to the retractor main body 30 in a right screw direction (clockwise direction when the converter 20 is viewed from the upper surface), the engagement projection 26 is locked by coming into contact with the locking piece 36a. Specifically, when the converter 20 is rotated in an axial rotation direction (clockwise direction) with respect to the retractor main body 30, the engagement projection 26 is gradually pressed down by the slope portion 36c and the converter 20 is fastened to the retractor main body 30 (second fixing member 38). When the converter 20 is further rotated in the clockwise direction, the engagement projection 26 advances over the slope portion 36c to reach the notched recess 36b. Here, since the peripheral length of the notched recess 36b is longer than the peripheral length (width direction) of the engagement projection 26, the engagement projection 26 is fitted into the notched recess 36b. When the converter 20 is further rotated in the clockwise direction, the engagement projection 26 is locked to the locking piece 36a in a state where the engagement projection 26 is fitted to the notched recess 36b (refer to FIG. 1B). The second fixing member 38 is generally reinforced in the radial direction by the rib 36d and the engagement projection 26 of the converter 20 is locked to the locking piece 36a by being reliably fitted to the notched recess 36b. For this reason, according to the medical treatment tool 10 of the present embodiment, a user can lock the converter 20 to the retractor main body 30 while feeling that the converter 20 is fastened. For this reason, it is possible to confirm a mounting angle while installing the converter 20, and in other words, it is possible to prevent incorrect installation of the converter 20 in which the ports 22a to 22d are located at an unexpected arrangement position.

In contrast, when the converter 20 is rotated around the axial direction of the retractor main body 30 in a reverse rotation direction (counterclockwise direction), the lock is released by the engagement projection 26 passing through the notched recess 36b, and thereby the converter 20 can be separated from the retractor main body 30 (refer to FIG. 1A). By disposing the engagement projection 26 and the locking piece 36a in four sites at intervals of 90 degrees, the converter 20 can be installed on the opening end 32 (second fixing member 38) of the retractor main body 30 at an installation angle which is selectively selected from a plurality of angles (four angles).

As shown in FIGS. 3A and 3C, the ports 22a to 22d are respectively provided with a plurality of valve members 24 and 25 through which the treatment tool can be inserted. The valve members 24 and 25 are respectively provided to upper edge sides and lower edge sides of the ports 22a to 22d. In each port, the valve member 24 and the valve member 25 are disposed apart from one another. The valve member 24 is provided further in an upper end side than the valve member 25. The valve members 24 and 25 have insertion holes through which the treatment tools are inserted and flaps that close the insertion holes in a natural condition. For example, the valve member 24 is a sheet valve where the insertion hole is opened and the valve member 25 is a duck bill valve or a cross valve. The insertion hole of the valve member 24 is a circular hole and isotropically contracts and extends in the radial direction. Since the valve member 25 is the duck bill valve or the cross valve, the valve member 24 contracts and extends in a particular direction or two particular directions. That is, the opening and closing direction of the valve member 24 and the opening and closing direction of the valve member 25 are different from each other (not the same as each other). Accordingly, there is no case where both of the valve members are separated from the treatment tool at the same time from the state where the valve members 24 and 25 are closely attached to the periphery of the treatment tool. Accordingly, degasification from the periphery of the treatment tool is favorably prevented when performing various treatments under the pneumoperitoneum. In addition, the valve members 24 and 25 support the treatment tool and act as a fulcrum during the handling. In particular, the treatment tool is handled during the surgery by having the valve member 24 in a high position projected upward from the top plate portion 21 as the fulcrum.

The top plate portion 21 is a flat membranous member having flexibility. With the top plate portion 21 being flexibly deformed, the ports 22a to 22d are displaced. For this reason, in a single hole-type surgery, it is possible to freely operate the positions and the directions of the treatment tools which are inserted into the ports 22a to 22d.

It is possible to choose the material of the top plate portion 21 and the valve members 24 and 25 from hard resins such as vinyl chloride resins, polyurethane resins, polyethylene resins, polypropylene resins, polyacetal resins, polycarbonate resins, polysulfone resins, or synthetic rubber such as silicone rubber, natural rubber, and nitrile rubber. It is preferable that the material of the valve members 24 and 25 be harder than the material of the top plate portion 21. Accordingly, when handling the treatment tool inserted into the cylindrical portion 23, the ports 22a to 22d are allowed to be displaced due to the top plate portion 21 being bent while maintaining the valve members 24 and 25 closely attached to the periphery of the treatment tool. For this reason, according to the medical treatment tool 10 of the present embodiment, it is possible to freely operate the treatment tool while maintaining the pneumoperitoneum condition of the patient. It is preferable that the durometer A hardness of the valve members 24 and 25 be higher than the durometer A hardness of the top plate portion 21 as an indication that the material of the valve members 24 and 25 is harder than the material of the top plate portion 21. More specifically, it is preferable that the durometer A hardness of the valve members 24 and 25 be greater than or equal to 40 and less than or equal to 70, the durometer A hardness of the top plate portion 21 be greater than or equal to 30 and less than or equal to 60, and the durometer A hardness of the valve members 24 and 25 be relatively higher than the durometer A hardness of the top plate portion 21. The durometer A hardness of the valve members 24 and 25 and the top plate portion 21 can be measured through the method defined by JIS K6253 and ISO 7619.

Examples of the treatment tools can include forceps for hold, scalpel for excision, auxiliary forceps, optical devices, and a trocar (cannula) for inserting these, but the treatment tools are not limited thereto.

Figure 4:
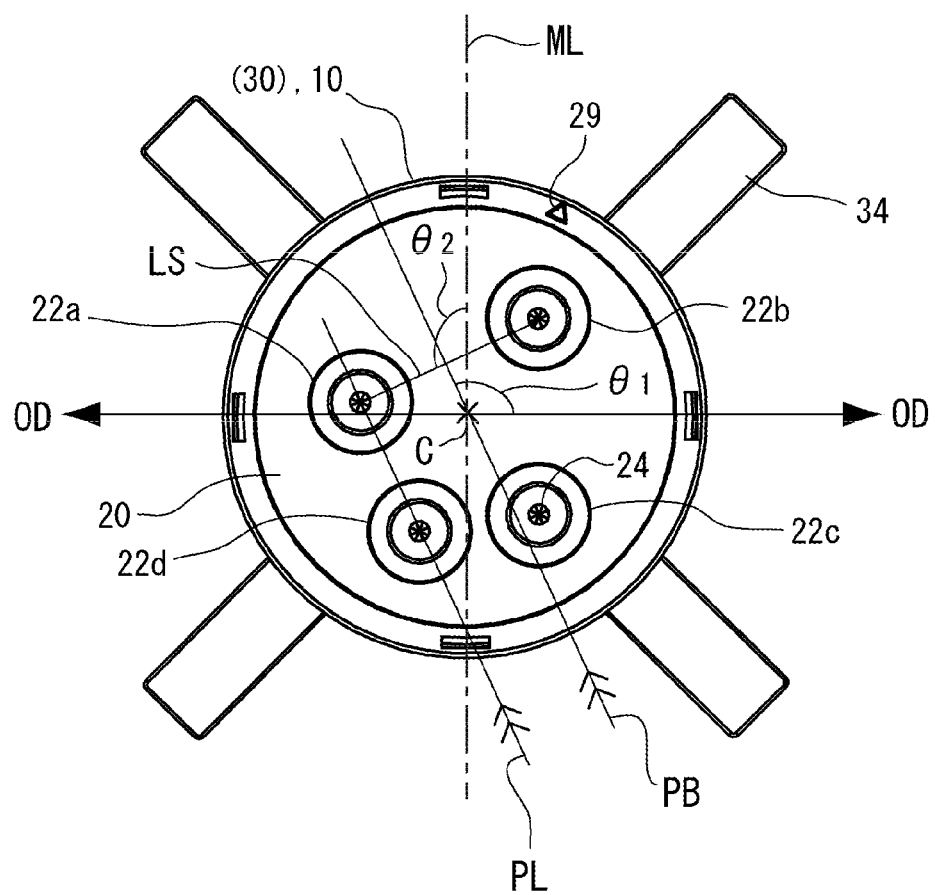
FIG. 4 is a plan view of the medical treatment tool in a state of being placed.

The arrangement of the ports 22a to 22d of the present embodiment will be described. FIG. 4 is a plan view of the medical treatment tool 10 in a state of being placed and corresponds to FIG. 2C. However, the incision INC is not shown in the drawing. The ports 22a to 22d disposed clockwise as shown in FIG. 4A are referred to in order as a first port to a fourth port.

The converter 20 includes at least a first port 22a to a third port 22c which are disposed in an approximately equilateral triangle shape. As described above, the installation angle of the converter 20 with respect to the retractor main body 30 is selected from the four or more installation angles (four installation angles in the present embodiment). For this reason, by converting the installation angle of the converter 20 in four ways, the direction of the triangle drawn by the first port 22a, the second port 22b, and the third port 22c is changed in the four ways.

In the medical treatment tool 10 of the present embodiment, the positional relationship between the ports 22a to 22d with respect to the retractor main body 30 differs in the respective installation angles which are selectively selected from the plurality of angles (four angles at maximum). The positional relationship between the ports 22a to 22d with respect to the retractor main body 30 may differ in any two angles among the maximum of the four angles. It is more preferable that the positional relationship between the ports 22a to 22d with respect to the retractor main body 30 differs among all of the plurality of angles (four angles) as shown in the present embodiment.

The point that the first port 22a to the third port 22c are disposed in an approximately equilateral triangle indicates that a third apex of the equilateral triangle, a line segment LS that connects centers of two arbitrary ports being one side of the triangle in the plan view of the converter 20 shown in FIG. 4, is located inside the other port. Specifically, in the present embodiment, the third apex of the equilateral triangle in which the center of the first port 22a is regarded as a first apex and the center of the second port 22b is regarded as a second apex is located inside the third port 22c. It is more preferable that the third apex be located inside the valve member 24 or 25 (refer to FIG. 4).

In the plan view of the converter 20, a perpendicular bisector PB of the line segment LS that connects the first port 22a and the second port 22b passes through the third port 22c. In other words, the third port 22c is located on the perpendicular bisector PB of the line segment LS that connects the first port 22a and the second port 22b.

In addition, the converter 20 has a fourth port 22d on a straight line (parallel line PL) which passes through the first port 22a and is parallel to the perpendicular bisector PB. In other words, the parallel line PL passes through the fourth port 22d in the plan view of the converter 20.

That is, the retractor main body 30 of the present embodiment includes an expansion unit (tension belt 34) that holds the incision INC expanded in a predetermined opening direction OD. In the plurality of installation angles, the positional relationships between the ports 22a to 22d with respect to the opening direction OD of the incision INC are different from each other. In other words, a quadrangle in which the center of each of the ports 22a to 22d are regarded as apexes in a case where the converter 20 is locked at a certain installation angle to the retractor main body 30 fixed to the incision INC is not completely coincident with the quadrangle in a case where the converter 20 is locked at other installation angle to the retractor main body 30. The converter 20 and the retractor main body 30 of the present embodiment are mutually locked at the four installation angles. All of the above-described quadrangles in the four installation angles are different from each other. Accordingly, it is possible to select the arrangement of the ports which is the most suitable to the diseased area to be treated from the plurality of angles, being four angles in the present embodiment.

The reason that the above-described arrangement of the first port 22a to the fourth port 22d is preferable will be described.

In the single hole-type surgery, forceps for hold may be inserted into one of two ports equally and directly facing the organ (diseased area) to be treated, and scalpel for excision may be inserted into the other one thereof. By lifting the object organ by holding it using the forceps, the organ is imparted with tension and the excision using the scalpel is favorably performed. Accordingly, in the case of the present embodiment, the treatment of the diseased area is favorably performed by locating the diseased area to be treated on the perpendicular bisector PB of the line segment LS that connects the first port 22a and the second port 22b. In cases where instruments such as medical clips are placed in the diseased area or the diseased area is sutured, similarly to the case of excising the diseased area, the forceps for hold may be inserted through one port and an other treatment tool may be inserted through the other port which is directly facing the organ and in parallel to the one port.

In contrast, in the single hole-type surgery, it is preferable to insert the optical device such as a charge coupled device (CCD) camera at a position where the visual filed is not blocked by the treatment tools inserted through the two ports. In the medical treatment tool 10 of the present embodiment, by disposing the third port 22c on the perpendicular bisector PB of the line segment LS, it is possible to insert the optical device in a position which is approximately equally separated from the first port 22a and the second port 22b.

Furthermore, by disposing the fourth port 22d in a position where the fourth port is separated from both of the first port 22a and the third port 22c, the interference between the treatment tools is suppressed. For this reason, the fourth port 22d is formed between the first port 22a and the third port 22c. In other words, the fourth port 22d is formed on the rear side of the first port 22a along the perpendicular bisector PB, that is, on the parallel line PL and on the same side as the third port 22c with respect to the line segment LS.

Here, it is necessary to obtain a wide movable range of the treatment tools by sufficiently expanding the incision INC while reducing the burden on the patient by reducing the length of the incision as much as possible. From such a viewpoint, it is preferable to make the shape of the incision INC in a straight shape, and then, to expand the incision in a radial shape using the retractor main body 30. In a case where the incision INC is made in a cross shape, the incision INC is expanded in a square shape in which the four end points of the cross shape are regarded as the apexes.

It is possible to install the retractor main body 30 at an arbitrary angle with respect to the incision INC. FIGS. 2 and 4 show a state where a straight line shaped incision INC (not shown) is formed in the abdominal wall along the median line ML and the retractor main body 30 is fixed to the incision INC such that the axial center C of the medical treatment tool 10 is coincident with the center of the incision INC.

At this time, the four tension belts 34 fix the retractor main body 30 to the incision INC at an angle where the four tension belts are disposed at a mirror-image symmetric position with the median line ML as a symmetric axis. In other words, the medical treatment tool 10 is fixed to the abdominal wall such that the tensile directions of the tension belts 34 are mirror-image symmetrical with respect to the median line ML.

Then, by simultaneously or sequentially pulling the four tension belts 34 in a state where the retractor main body 30 is fixed to the incision INC, the diameter of the incision INC is expanded in the opening direction OD which is a direction perpendicular to the median line ML.

The converter 20 is installed on the opening end 32 of the retractor main body 30 fixed to the incision INC, at a mounting angle selected from the plurality of angles (four angles in the present embodiment).

It is preferable that the angle $\Theta_1$, which is formed between the perpendicular bisector PB of the line segment LS that connects the first port 22a and the second port 22b and the opening direction OD of the incision INC when the converter 20 is installed on the opening end 32 at any one or more installation angles (refer to FIG. 4), be 115 degrees ±20 degrees, that is, greater than or equal to 95 degrees and less than or equal to 135 degrees. In addition, it is preferable that the angle $\Theta_2$, which is formed between the line segment LS that connects the first port 22a and the second port 22b and the median line ML, be 115 degrees ±20 degrees. Furthermore, it is more preferable that the angles $\Theta_1$ and $\Theta_2$ be 115 degrees ±10 degrees, that is, greater than or equal to 105 degrees and less than or equal to 125 degrees. In the case of the present embodiment, the opening direction OD and the median line ML are perpendicular to each other and the perpendicular bisector PB and the line segment LS are perpendicular to each other, and therefore, the angles $\Theta_1$ and $\Theta_2$ are identical.

The angles $\Theta_1$ and $\Theta_2$ referred herein are directed angles. The angle $\Theta_1$ is an angle measured in the counterclockwise direction starting from the right side of a body BOD of the patient as a reference (0 degrees), to the perpendicular bisector PB. The angle $\Theta_2$ is an angle measured in the counterclockwise direction starting from the direction which faces the head in the median line ML from the axial center C (umbilicus) of the medical treatment tool 10 as a reference (0 degrees), to the line segment LS.

By setting the angles $\Theta_1$ and $\Theta_2$ to 115 degrees ±20 degrees, the medical treatment tool 10 of the present embodiment is particularly favorable in treatment of the gallbladder GB. The reason will be described with reference to FIGS. 5 and 6.

Figure 5:
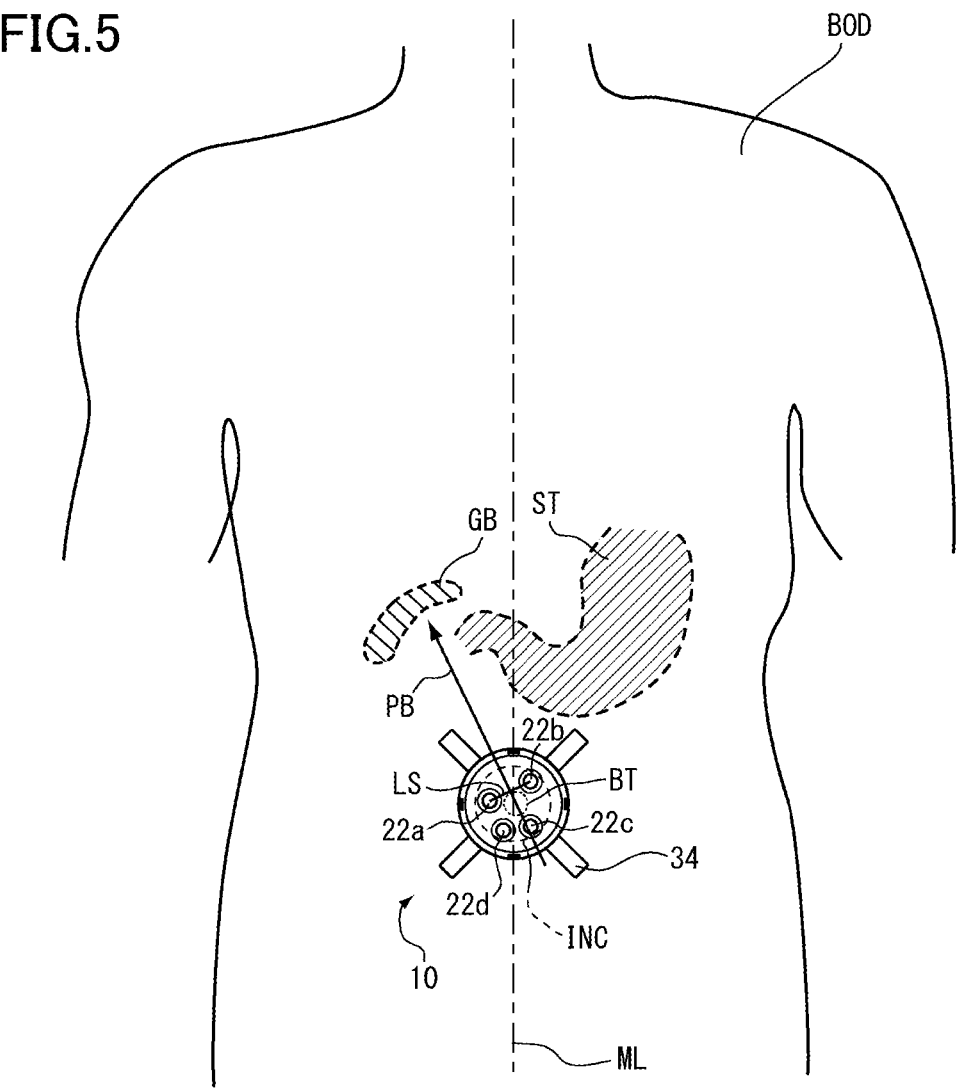
FIG. 5 is a schematic diagram showing a state where the medical treatment tool is placed at a first mounting angle.

FIG. 5 is a schematic diagram showing a body BOD of a patient. The gallbladder GB and the stomach ST are schematically shown in FIG. 5. The incision INC is formed on the median line ML of the body BOD and the retractor main body 30 is placed in the incision INC at the same mounting angle as those in FIGS. 2C and 4. Specifically, the opening direction OD of the incision INC is coincident with the perpendicular direction (left side direction and right side direction of the body BOD) of the median line ML. The mounting angle (hereinafter, referred to as a first mounting angle) of the converter 20 on the retractor main body 30 is also the same as those in FIGS. 2C and 4.

Figure 6:
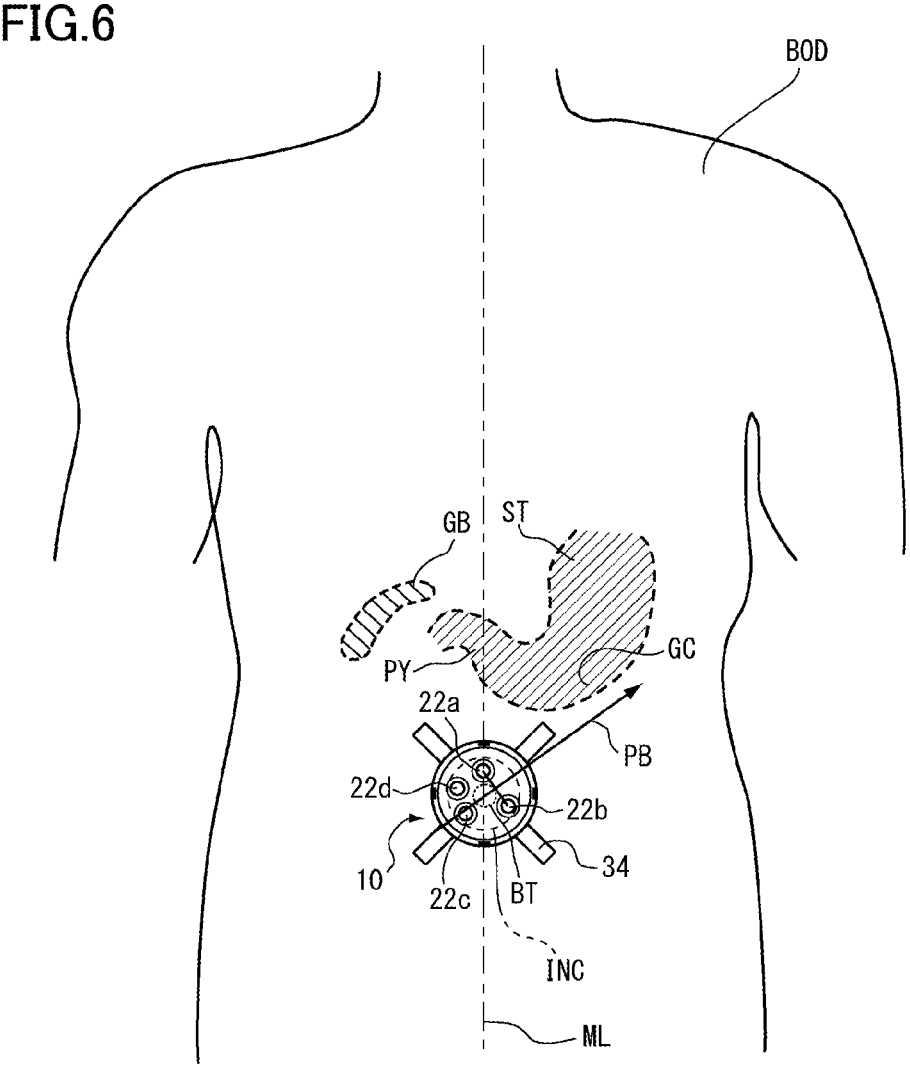
FIG. 6 is a schematic diagram showing a state where the medical treatment tool is placed at a second mounting angle.

FIG. 6 shows a state where the converter 20 is fixed to the retractor main body 30 by selecting the other mounting angle (hereinafter, referred to as a second mounting angle) while the retractor main body 30 is fixed to the incision INC. More specifically, the second mounting angle shown in FIG. 6 is an angle where the first mounting angle shown in FIG. 5 is advanced 90 degrees clockwise.

As described above, in the first mounting angle shown in FIG. 5, the angle $\Theta_1$, which is formed between the perpendicular bisector PB of the line segment LS that connects the first port 22a and the second port 22b and the opening direction OD of the incision INC by the tension belt 34, is 115 degrees ±20 degrees. Then, in a typical use of the medical treatment tool 10 shown in FIG. 5, the extending direction of the perpendicular bisector PB when the converter 20 is installed at the first mounting angle is oriented towards the gallbladder GB. In FIG. 5, the retractor main body 30 is placed on the incision INC formed along the median line ML with the umbilicus BT as a center such that the opening direction OD by the tension belt 34 is made coincident with the perpendicular direction of the median line ML. Accordingly, the medical treatment tool 10 in which the converter 20 is provided at the first mounting angle as shown in FIG. 5 is suitable in treatment of the gallbladder GB since it is possible to respectively insert the forceps and the scalpel through the first port 22a and the second port 22b which are equally facing the gallbladder GB. That is, in the first mounting angle, it is possible to lift the gallbladder GB by inserting the forceps for hold through the first port 22a and to favorably excise the ductus cysticus of the gallbladder GB by inserting the scalpel through the second port 22b.

The extending direction of the perpendicular bisector PB when the converter 20 is installed on the retractor main body 30 at the second mounting angle is oriented towards the greater curvature GC of the stomach ST as shown in FIG. 6. For this reason, according to the medical treatment tool 10 in which the converter 20 is provided at the second mounting angle, it is possible to favorably treat the stomach ST from the pylorus PY to the greater curvature GC using the forceps and the scalpel which are inserted through the first port 22a and the second port 22b.

Since the perpendicular bisector PB is oriented to the vicinity of the rectum at a third mounting angle where the perpendicular bisector is further advanced 90 degrees clockwise from the second mounting angle, it is possible to favorably perform treatment of the rectum using the treatment tools inserted through the first port 22a and the second port 22b. Furthermore, since the perpendicular bisector PB is oriented to the large intestine at a fourth mounting angle where the perpendicular bisector is further advanced 90 degrees clockwise from the third mounting angle, it is possible to favorably perform treatment of the large intestine using the treatment tools inserted through the first port 22a and the second port 22b.

That is, according to the medical treatment tool 10 of the present embodiment, it is possible to favorably perform the single hole-type surgery on a plurality of organs such as the gallbladder GB, the stomach ST and the like which are exemplified above as objects to be treated by selecting the mounting angle of the converter 20 with respect to the retractor main body 30 from the plurality of angles. In addition, since the converter 20 is detachable from the retractor main body 30, it is possible to take out the excised tissue through the opening end 32 having a large diameter by removing the converter 20 from the retractor main body 30 after the excision of the organ. Therefore, according to the medical treatment tool 10 of the present embodiment, it is possible to further perform a series of operations of taking out the organs by changing the operation under the pneumoperitoneum performed while the converter 20 is installed to an operation under direct vision performed after removing the converter 20.

According to the present embodiment, when the converter 20 which is once removed is installed again on the retractor main body 30, the positional relationship between the ports 22a to 22d and the organs is reproduced in so far as a common mounting angle is selected. This is because the converter 20 is fixed to the retractor main body 30 at the identical position using the engagement projection 26 and the locking portion 36 (locking piece 36a).

Here, an indicator portion 29 (refer to FIG. 4) is provided in the medical treatment tool 10 of the present embodiment so as not to erroneously change the selection of the mounting angle in a case of repeatedly installing the converter 20 on the retractor main body 30.

Figure 7A:
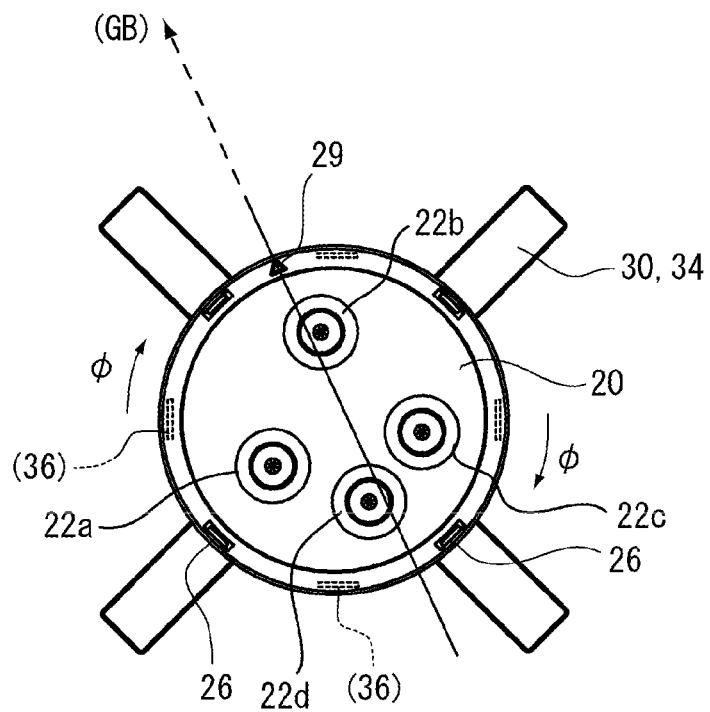
FIG. 7A is a plan view showing a non-locked state where the converter comes into contact with the opening end.
Figure 7B:
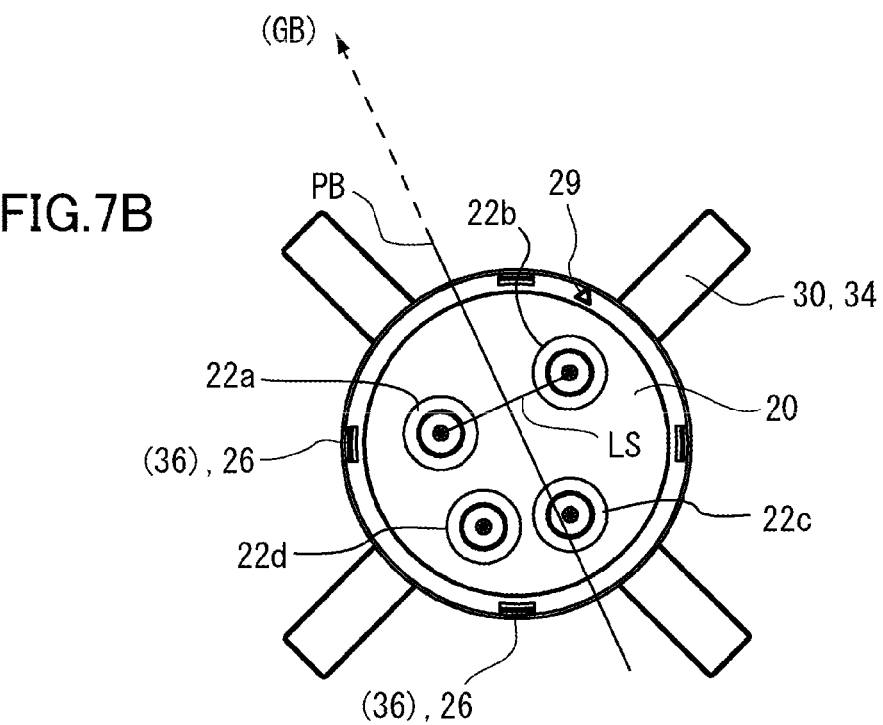
FIG. 7B is a plan view showing a locked state where the converter is locked to the retractor main body.

FIGS. 7A and 7B are plan views describing a method of installing the converter 20 performed using the indicator portion 29.

FIG. 7A shows an unlocking state where the converter 20 comes into contact with the opening end 32. FIG. 7B shows a locking state where the converter 20 is locked to the retractor main body 30. The converter 20 becomes the locking state shown in FIG. 7B by rotating the converter 20 with respect to the retractor main body 30 in an axial rotating direction (clockwise direction in the present embodiment) by a predetermined angle $\phi$ from the unlocking state of FIG. 7A. In the locking state, the locking units (engagement projection 26 and locking portion 36) lock the converter 20 to the retractor main body 30.

The unlocking state is a state where the locking units (engagement projection 26 and locking portion 36) are not engaged and is a state where the converter 20 temporarily comes into contact with the retractor main body 30. Various specific unlocking states can be employed, but the medical treatment tool 10 of the present embodiment shows in FIG. 7A a state where the engagement projection 26 of the converter 20 and the locking portion 36 of the retractor main body 30 are deviated from each other to the maximum. In other words, the unlocking state shown in FIG. 7A is a state where the engagement projection 26 and the locking portion 36 are separated from each other at intervals of 45 degrees and the above-described predetermined angle $\phi$ is 45 degrees.

Here, the indicator portion 29 shows the extending direction of the perpendicular bisector PB in the locking state shown in FIG. 7B. The indicator portion 29 is provided further forward than perpendicular bisector PB in the axial rotating direction (clockwise direction) by a predetermined angle $\phi$. That is, the direction shown by the indicator portion 29 in FIG. 7A in which the converter 20 temporarily comes into contact with the retractor main body 30 is coincident with the direction in which the perpendicular bisector PB is oriented in FIG. 7B in which the converter 20 is installed on the retractor main body 30.

Accordingly, before installing the converter 20, it is possible to confirm the arrangement position of the ports 22a to 22d in advance when the converter 20 is finally installed on the retractor main body 30 in a case where the converter 20 is repeatedly attached to or detached from the retractor main body 30 to takeout the excised tissue (gallbladder GB) from the incision INC, or the like. Accordingly, it is possible to avoid the burden on the patient due to re-installation by preventing erroneous selection of the mounting angle of the converter 20.

The indicator portion 29 of the present embodiment is a direction indication mark provided in the vicinity of the outer circumference of the top plate portion 21 of the converter 20, but this is merely an example. Other examples of the indicator portion 29 may include a configuration capable of identifying the direction of the angle of the converter 20 using color, character display, or the like.

The present invention is not limited to the above-described embodiments and various modes such as deformation or improvement are included as long as the object of the present invention is achieved.

Figure 8:
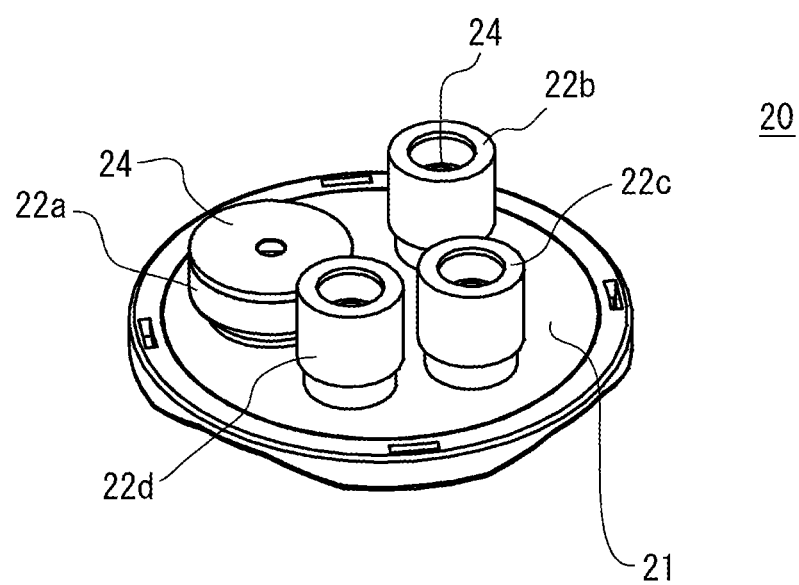
FIG. 8 is a perspective view of a converter according to a modification example when seen from above.

FIG. 8 is a perspective view of a converter 20 according to a modification example when seen from above. The converter further has another port (fourth port 22d) on a straight line (parallel line PL) which passes through a first port 22a and is parallel to a perpendicular bisector PB. The formation height of a valve member 24 of the fourth port 22d is different from the formation height of the valve member 24 of the first port 22a. In other words, in the converter 20, the formation heights of the valve member 24 in a high position with respect to the top plate portion 21 are different in the first port 22a and the fourth port 22d. Here, the valve member 24 becomes a fulcrum for treatment tools inserted through the ports 22a to 22d. Accordingly, by differentiating the height of the fulcrum in the first port 22a and the fourth port 22d which are adjacently aligned in the extending direction of the perpendicular bisector PB, interference between the treatment tools is favorably prevented.

To be more specific, the height of the projection of the first port 22a from the top plate portion 21 is lower than those of the second port 22b to the fourth port 22d. Accordingly, the movable range of the treatment tool inserted through the first port 22a is increased. For the same reason, the movable range of the base end of the treatment tool may be further increased by increasing the diameter of the first port 22a more than that of the fourth port 22d.

The invention claimed is:

1. A medical treatment tool comprising:
    a cylindrical retractor main body which is capable of being placed in an incision;
    a converter which is detachably installed on an opening end of the retractor main body to close the opening end; and
    ports which are provided in a plurality of sites of the converter and through which treatment tools are inserted into the retractor main body,
    a locking unit that locks the converter to the retractor main body to be in a locking state by rotating the converter in an axial rotating direction with respect to the retractor main body by a predetermined angle from a non-locking state where the converter comes into contact with the opening end,
    wherein the converter can be installed on the opening end at an installation angle which is selected from a plurality of installation angles, and positional relationships of the ports with respect to the retractor main body when the converter is installed on the opening end at the respective installation angles become different from each other,
    wherein the retractor main body includes an expansion unit that is capable of holding said incision in an expanded state in a predetermined opening direction, and
    wherein in the plurality of installation angles, positional relationships of the ports with respect to the incision in the opening direction are different from each other,
    wherein the locking unit:
    locks the converter to the retractor main body to be in a locking state at a first installation angle;
    locks the converter to the retractor main body to be in a locking state at a second installation angle that is an angle where the first installation angle is advanced clockwise by a first angle;
    wherein an angle, which is formed between a perpendicular bisector of a line segment that connects a first port and a second port and the opening direction when the converter is installed on the opening end at the first installation angle, is 115 degrees ±20 degrees.

2. The medical treatment tool according to claim 1, further including at least the first port to a third port disposed in an approximately equilateral triangle shape and the installation angles are selected from four or more angles.

3. The medical treatment tool according to claim 1, wherein a plurality of valve members capable of inserting the treatment tools are respectively provided in the ports.

4. The medical treatment tool according to claim 3, wherein the converter includes a flexible top plate portion that closes the opening end,
    wherein the top plate portion is provided with the first port and the second port, and
    wherein the valve member is made of a harder material than that of the top plate portion.

5. The medical treatment tool according to claim 3, further comprising:
    another port, of which the formation height of the valve member is different from the first port, said another port being disposed on a straight line which passes through the first port and is parallel to the perpendicular bisector.

6. The medical treatment tool according to claim 1, wherein an indicator portion that shows an extending direction of the perpendicular bisector in the locking state is provided further forward than the perpendicular bisector in the axial rotating direction by the predetermined angle.

7. The medical treatment tool according to claim 1, wherein the first angle is 90 degrees.

* * * * *